United States Patent [19]
Alt

[11] Patent Number: 5,116,605
[45] Date of Patent: May 26, 1992

[54] COMPOSITION AND SKIN TREATMENT METHOD THEREWITH FOR MITIGATING ACNE AND MALE-PATTERN BALDNESS

[76] Inventor: John P. Alt, 616 NE. 11th Ave., Fort Lauderdale, Fla. 33304

[21] Appl. No.: 803,178

[22] Filed: Dec. 5, 1991

Related U.S. Application Data

[63] Continuation-in-part of Ser. No. 527,813, May 24, 1990, which is a continuation-in-part of Ser. No. 321,216, Mar. 9, 1989, abandoned.

[51] Int. Cl.⁵ .................. A61K 7/06; A61K 7/075
[52] U.S. Cl. ............................ 424/70; 424/680; 514/859; 514/864; 514/880; 514/881
[58] Field of Search ............... 424/70, 680; 514/859, 514/880, 881, 864

[56] References Cited

U.S. PATENT DOCUMENTS

| | | | |
|---|---|---|---|
| 4,174,296 | 11/1979 | Kass | 424/70 |
| 4,515,778 | 5/1985 | Kastell | 424/70 |
| 4,660,580 | 4/1987 | Hoch et al. | 424/70 |

Primary Examiner—Thurman K. Page
Assistant Examiner—Amy Hulina
Attorney, Agent, or Firm—Herbert L. Lerner; Laurence A. Greenberg

[57] ABSTRACT

A topical application composition for mitigating male pattern baldness and testosterone-induced acne contains, as essential active, androgen-reducing components (a) a testosterone-reducing amount of an ionizable sodium salt, and (b) an association of compounds for forming, androgen segregating cellular proliferation phospholipids. The association includes lecithin, soy oil, phosphoric acid, choline chloride and optionally inositol and a nonionic surfactant in an amount for solubilizing and/or dispersing components (a) and (b) in a cosmetically-compatible vehicle for topical application.

13 Claims, No Drawings

COMPOSITION AND SKIN TREATMENT METHOD THEREWITH FOR MITIGATING ACNE AND MALE-PATTERN BALDNESS

CROSS-REFERENCE TO RELATED APPLICATIONS

This application is a continuation-in-part of application Serial No. 527,813, filed May 24, 1990 which is a March 9, 1989.

FIELD OF THE INVENTION

This application relates to compositions for mitigating acne and male-pattern baldness and skin treatments therewith and more particularly to such compositions containing both ionic and enyzmatic components for neutralizing the excess of androgens causing these conditions.

BACKGROUND OF THE INVENTION

It is well established that both acne and male-pattern baldness are the result of accumulation of androgens, particularly testosterone and dihydrotestosterone.

Acne begins at puberty when the increase in circulating androgens causes an increase in size and activity of the pilosebaceous glands.

Male-pattern baldness is common and it is well-recognized to be familial and proven to require the presence of androgens. (Merck Manual 15th Ed.pg. 2277 and 2281) It is recognized that circulating testosterone is metabolized in the skin to dihydrotestosterone (DHT) (Benson et al U.S. Pat. No. 4,088,760) which is 4 to 20 times as potent an androgen as testosterone.

It is postulated that the varying rates of formation and high accumulations of DHT in the skin give rise to the pathogenesis of acne and other androgen-related conditions, particularly male-pattern baldness.

Male-pattern baldness, wherein hair follicles, primarily on the crown of the head, shrink in size, producing an ever thinner and thinner hair until ultimately many follicles shrink to a point where they no longer can produce a hair, i.e., they become dormant. Individuals showing male-pattern baldness begin to lose their hair early in life, often in their twenties. It is well documented that male-pattern baldness is a type of sex-influenced inheritance, with the allele for pattern baldness being dominant in males and recessive in females. The precise mechanism of androgen conversion and toxic accumulation is not thoroughly understood.

Over the past several years, extracellular androgen-binding macro molecules have been identified that are distinct from the intracellular androgen-receptors. The best characterized are the testosterone-extradiol binding globulin (TeBG) from serum and the androgen binding protein (ABP) from the testes, as disclosed in "Extracellular Androgen Binding Proteins" by Bardin et al in Ann.Rev. Physiol, 1981, pages 189-198. A variety of in vivo studies have suggested that TeGB-bound testosterone is less available for expression of biological activity than is the free steroid.

Although the absence of localized accumulation of androgens is believed fundamentally necessary to counter acne and expression of baldness in males, other factors are also important.

Basically, there are different methods by which such biochemical activities are controlled. One, as mentioned, is genetic regulation and accumulation and enzymatic regulation as well. Most often these regulatory mechanisms function as feedback control systems that continually monitor a cell's biochemistry and make corrections as needed. But, on occasion, substances from without also control intracellular biochemical reactions, by inhibiting or activating one or more of the intracellular control systems.

One such controlling extrinsic factor is the topical application of ionizable salts to disassociate the testosterone or DHT. Such ionizable salts effect changes in the hormones or protein-associated hormones. Such effects include interrupting the hormone-protein linkages as well as breaking the complex structures to inactivate the active androgenic components of these molecules. Removal or inactivation of the active androgenic elements removes the toxic effects of the androgens, testosterone and/or DHT, the congestion at the hair follicles leading to clinical acne and/or male pattern baldness.

A number of researchers have postulated that phospholipid metabolism may be a factor in cellular proliferation and follicular metabolism (Yu and Tsai et al of Roche Institute) Cell Vol 52 p.63-71 1988 and Science V 243 p 522-25; V 250 p.982-84. The phospholipids activate guanosine triphosphatase (GTPase) which decomposes or otherwise inactivates testosterone and/or DHT. Suitable phospholipids, for example, include complexes of lecithins, complexed with saturated and unsaturated fatty acids or oils containing some inositol and nitrogenous bases such as choline and choline chloride. Phosphoric acid in small amounts insures the stability of such complexes when topically applied.

THE INVENTION

It is an object of this invention to provide topical compositions for the mitigation of acne and male-pattern baldness and methods and regimens for the application of these compositions to the skin to remove, decompose or degrade accumulations of those androgens causing these conditions.

It is another object of this invention to provide such compositions that combine ionic androgen-decomposing components with complexed phospholipid androgen-inhibiting components that mitigate said conditions.

Other ancillary objects are provided by the inclusion within the compositions and treatments of this invention, of cosmetic ingredients for localized application and contacting the actives of this invention with the affected hair follicles and sebaceous glands causing the male-pattern baldness and acne.

These and other objects are achieved by this invention which provides compositions for topical application to said affected hair follicles and affected sebaceous glands containing as essential actives a) a testosterone-reducing amount of an ionizable sodium salt and b) an association of compounds for forming cellular proliferation phospholipids, said association consisting essentially of lecithin, soy oil, phosphoric acid, choline chloride and, optionally, inositol.

The testosterone-reducing ionizable salt and the phospholipid complex are rendered compatible by the inclusion in the composition of a topically-acceptable surfactant that will disperse these ionizable salts and the phospholipid complexes through the compositions of the invention. Suitable dispersants are the polysorbates with chain lengths selected for adequate dispersability of the components in the aqueous vehicle.

Also within the scope of the invention, are the operative and optimal ranges for the stated active components.

The compositions of the invention, in addition, may contain topical and cosmetic adjuvants for preparing the skin surfaces to accept the actives, to assist the action of the actives, to stabilize the components in the vehicle and to render the composition aesthetically acceptable to the user.

DETAILED DESCRIPTION OF THE INVENTION

All parts, proportions and percentages are by weight unless otherwise stated. The exceptions are where liquid compositions are diluted to stated volumes i.e. "q.s. ad-"

The term "androgen" or "excess androgens" refers to those male hormones that, in excess at the skin or hair follicles, are implicated in the etiology of acne and male-pattern baldness. Specific examples are, testosterone and DHT.

The ionizable sodium salts are preferably, sodium chloride, the most readily available sodium salt, but other non-toxic sodium salts, preferably those that form approximately neutral solutions, will also serve. Among such salts, are sodium fluoride, sodium citrate, etc., but the chloride is preferred. Potassium salts do not serve as ionizable components for this invention.

Lecithin as used herein, refers to the liquid, aminophosphotides found as the waxes in animal and vegetable tissue. They are esters of glycerol or glycerophosphoric acid with naturally occurring saturated and unsaturated fatty acids and choline. It is commercially available from egg yolks and soya beans. The latter source is preferred. It is a lipotropic surfactant and emulsifier and may serve in this invention to prevent the formation or accumulation of 5-alphareductase. This latter enzyme has been implicated in the conversion of testosterone to the much more potent—dihydrotestosterone. Alternatively, it may isolate, at the follicle level, any excess of these androgens and mitigate their activity of causing the male-pattern baldness and acne.

These specific effects of the androgens is very complex but indirectly supports the premise of the invention by the well observed increases in acne and male-pattern baldness among anabolic steroid users and abusers.

As the lecithins are glycerophosphatides esterified with choline, which are insoluble in water, lipotropic and subject to oxidation, it is useful to stabilize them in the compositions of this invention, by including stabilizing amounts of phosphoric acid, soya oil and choline chloride in the formulations.

Additionally, extra choline as the chloride is included as choline has recognized vasodilating properties and is involved in the mechanism of cell permeability.

Inositol is a part of the vitamin B-complex. It is water souble but lipotropic. It is found in nature as phytic acid, a glycophosphotide. It is an optional ingredient useful in those compositions, according to this invention, for male-pattern baldness. The reasoning behind the optional inclusion of inositol within the ambit of certain aspects of this invention, is its lipotroptic phosphotide prolivity and its proven in vivo activity in various species, as a growth factor and particularly that its absence in certain species causes alopecia.

It clearly is a growth factor and its extrinsic effect in human species, if often masked by its intrinsic synthesis in the human body. However, its presence in the formulation subjectively provides better improvement as compared to formulations where it is absent.

The preferred dispersant is the non-ionic polysorbate-80 (Merck Index 11th Ed. #7559), which is one of the class of non-ionic surface active dispersants and surfactants from complexed hexahydric alcohols esterified with alkylene oxides and fatty acids. Because of their lack of polarity, they are excellent dispersant for either ionic or non-polar materials. The polysorbate-80 is preferred as it is very water soluble and also is soluble in saturated and unsaturated fatty oils, alcohols, aromatic solvents and esters, such as ethyl acetate to form essentially neutral solutions. The pH of a 0.5% aqueous solution ranges from 5-7 pH. This Tween-80 type of surfactant is useful, as it permits both ionic materials such as the NaCl components and phospholipids to penetrate to the cell membranes of the skin being treated.

The components of this invention are active within specific concentration ranges as follows:

|  | % range |
|---|---|
| Component a) | |
| The ionizable sodium salt | |
| NaCl | 2.0–5.5 |
| Component b) | |
| The phospholipid complex | |
| lecithin | 0.35–3.5 |
| inositol | 0.0–3.0 |
| soya oil | 0.008–0.04 |
| phosphoric acid | 0.005–0.035 |
| choline chloride | 0.025–3.0 |
| Component c) | |
| The dispersant for a) and b) | |
| polysorbate -80 | 0.3–3.0 |

NaCl concentrations below the stated range appear ineffective. Concentrations of NaCl above the stated range are irritating. Depending on the dissociation constants of other Na salts, this range may be slightly expanded i.e. lowered for more highly ionized salts and raised for the less ionized salts.

The phospholipid concentration at lower than stated levels appears to be ineffective and at higher than the stated range, shows no greater advantage over the highest effective levels. This may be a function of accessibility or follicle penetration.

The phospholipid stabilizer ranges have been empirically estimated.

The minimum amount of polysorbate-80 is that necessary for combining the ionizable salt and the phospholipid. The stated upper limit is for non-shampoo formulations. Higher amounts of the polysorbate-80 will be found in the cleansing or shampoo formulas. This is in addition to the necessary amounts for the combination of the actives.

The formulation of this invention may optionally include vitamins that are topically active to maintain healthy skin. Among such optionally included vitamins are Vitamin E, the tocopherols; Vitamin D and its precursors; the above discussed inositol; the pantothenic acid now believed needed for activation of inositol; and the choline. The amounts listed for the vitamins are concentration per liter. The topical effects of these vitamins is just now being clarified.

Vitamin E is known for its healing qualities. Basis for this healing reputation is as an antioxident, preventing structural changes in the unsaturated lipid components of the cell membrane. It has also been shown to be involved in the regulation of lipid biosynthesis and has been noted to be involved in controlling the destructive action of free radicals on living tissue and organs. Its useful range in the compositions of this invention is from 25 to 150 international units (IU) per liter.

The preferred range is from 75 to 125 IU.

Vitamin D and its precursors have been shown to be important to the functioning of the invention. The effects of Vitamin D on calcium absorption is well known but its converse, its action on phosphate transport and absorption while recognized, is not yet too clear. It is believed that Vitamin D may act directly but more likely is its secondary effect, with the calcium acting as a transport mediator for the phosphate. The equivalence and equilibration of activities of the various vitamin D precursors is known in the literature. The range of Vitamin D is from 50 to 250 IU/liter with 100 IU to 175 IU as the preferred range.

Inositol has already been discussed and its activation by pantothenic acid has been noted.

The presence of vitamins and inositol is optional and they are included in the formulation of this invention as adjuvants for promoting the recovery of the sebaceous glands and hair follicles after the excess of androgens has been relieved.

In addition the topical compositions of this invention are preferably formulated as liquids for ease of application and penetration to the cellular level of involved skin tissue. More viscous liquid may be used for prolonged contact of the actives at the desired sites.

In general, the method aspects of this invention include the steps of applying the compositions containing the actives to the affected areas. Preferably, in male-baldness mitigation the compositions are applied initially via shampoo formulations containing the actives. The shampoo compositions are maintained in contact with the treated areas to cleanse them thoroughly and to contact the actives with the hair follicles. Contact is maintained for at least three minutes. After that time, shampoo may be rinsed from the skin and the actives may be reapplied in topical skin conditioner formulations that adhere to the affected area for more extended contact times.

The shampoos mentioned above contain the actives of this invention within the desired ranges suspended or dissolved in commercial shampoo bases. One such commercial shampoo base is CYCLORL-ALC-2 containing PEG-80 Sorbitan laurate, sodium trideceth sulfate, aluroamphoglyconate, Laureth-13 carboxylate, PEG-150 distearate, cocamidopropyl hydroxysultaine and citric acid dissolved in water, which is marketed by Cyclo Corporation, Miami, Florida, and has been the shampoo base used in the shampoo and scrub formulations of the examples.

The skin conditioner formulations contain the actives in aqueous solution. The solution of the actives may be formulated to provide the actives in the effective concentration ranges in vehicles modified to assure good contact with skin tissue for sufficient time for the actives to be adsorbed or absorbed and thus provide the stated androgen-modifying activity at the affected tissues and follicles.

The vehicle may be in liquid or semisolid form. The liquid may be aqueous solutions modified with thickeners and surfactants or as emulsions with the actives preferably distributed in the aqueous phase. However, the fat-soluble actives may be included in the oil phase. The emulsions may have various ingredients that make the emulsions substantive to the skin and the affected tissue to thus deposit the actives at the desired sites and to maintain activity in situ for extended times. Liposomes are a recent vehicle permitting such in situ deposition of androgen-modifying agents.

As with all skin products, it is important to satisfy the consumer so that any long term regimen for desired results will be followed. For this reason, it is useful to include in the compositions, colorants, odorants and emollients to form aesthetic and compatible formulations.

Such compatible ingredients are included within the scope of the invention.

The appended examples are exemplary of useful formulations and regimens herewith.

All art-recognized equivalents are intended.

| Shampoo Formulation | % |
|---|---|
| Shampoo Base (CYCLORL-ALC-2) | 35.5 |
| NaCl | 3.82 |
| Polysorbate -80 | 2.25 |
| Lecithin - soya | 2.78 |
| Soy Oil | 0.10 |
| Phosphoric acid | 0.25 |
| Choline chloride | 0.40 |
| Inositol | 0.25 |
| Vitamin D | 150 IU |
| Vitamin E | 100 IU |
| Water q.s. ad | 1.0 liter |

This composition is prepared by incorporating into the shampoo base, the polysorbate -80, the lecithin, soy oil, the vitamins and choline chloride to form a paste. The sodium chloride is then dissolved in the water to which is then added the inositol and the phosphoric acid. The NaCl solution is then slowly added to the paste with constant stirring until a uniformly dissolved composition is formed. A slight collodial quality is noted.

A portion (abt 1-3 cc) of the composition is spread into the previously wetted hair and scalp. This applied shampoo formulation is massaged in standard shampoo practice throughout the hair, scalp and affected areas to be cleansed. The massage is useful, in addition to its cleansing action, for stimulating the blood circulation to the cleansed areas contacted by the actives in the composition. The composition is maintained in contact with the skin in the desired areas (massage time included) for a total time of 3 to 5 minutes which is sufficient for initiation of interaction of the actives with the target androgens at the epitherial level.

At the end of this time (which may be exceeded) the formulation is rinsed from the contacted areas and then the compositions according to succeeding Examples, may be applied.

EXAMPLE 2

| Hair and Skin Conditioner | gm |
|---|---|
| Shampoo Base (CYCLORAL-AL(-2) | 1.15 |
| NaCl | 3.82 |
| Polysorbate -80 | 2.25 |
| Lecithin | 2.78 |
| Soy Oil | 0.10 |
| Phosphoric acid | 0.25 |
| Choline chloride | 0.40 |
| Inositol | 0.25 |
| Vitamin D | 150 IU |
| Vitamin E | 100 IU |

| Hair and Skin Conditioner | gm |
|---|---|
| Water qs ad | 1.0 liter |

The shampoo base, approximately 50 cc of the water, the polysorbate-80, lecithin, soy oil, the vitamins and choline chloride are incorporated to form a paste. The other ingredients, including the salt, are dissolved in the rest of the water. This solution is then slowly incorporated by agitation into the paste until a uniform solution results.

Two to four cc of this solution is used as an application to the cleansed and damp rinsed skin areas, resulting from the initial stages of the regimen as started in Example 1 (supra). After this application and light massage of the formulation into the affected areas of the skin, the areas are air dried.

The efficacy of the above regimen was evaluated on male-pattern baldness in more than 60 selected subjects of a total of 75 tested. Within one month of twice daily application of the regimen to the hairy and balding areas of the scalp, there occurred a substantial thickening of the hair in the crown area of the head as well as totally new hair growth, particularly filling out the hairline areas on the forehead. In the crown areas, an increase in hair numbers was noted.

After the initial one month observation period, the successful subjects were divided into three groups to evaluate the efficacy of the shampoo vs the conditioner and the complete regimen. Moderately further improvement was noted with either shampoo alone or blank shampoo with the conditioner of Example 2. But best results were obtained by daily application, at least once a day, of the active-containing shampoo followed by the active-containing conditioner.

In three years of testing of these actives in various vehicles and concentrations, there have been no reported deleterious side effects within the effective ranges.

EXAMPLE 3

| Facial Scrub for acne | % |
|---|---|
| Shampoo base - CYCLOR-AL-C2 | 35.5 |
| NaCl | 3.82 |
| Polysorbate -80 | 2.25 |
| Lecithin | 2.78 |
| Soy oil | 0.10 |
| Phosphoric acid | 0.25 |
| Choline chloride | 0.40 |
| Boric acid | 0.10 |
| Vitamin D | 150 IU |
| Vitamin E | 100 IU |
| Water q.s ad | 1.0 liter |

The composition is prepared by preparing a paste of the shampoo base, the lecithin, the polysorbate-80, soy oil, the vitamins and the choline chloride. A solution is prepared from the remaining ingredients including the boric acid. The solution is slowly introduced into the paste until completely dissolved. It will be noted that Boric acid replaces inositol in the formulation. Boric acid is a recognized topical antiseptic. Inositol, while active in alopecia, has no clinical or theoretical record in acne.

The scrub composition is used in the conventional manner. Between half to 2 cc is applied to the wet skin that has previously been rinsed with water. The foaming scrub is massaged into the skin either with the finger tips or cloths or mildly-abrasive, synthetic sponges. This scrub facilitates a deep cleansing action in the acne affected areas. Usually the locale is the face, but while not obvious, a major locale for acne is the back. While not a very hairy area, in adolescent males it is a very acne-prone area, but seldom in females where frontal areas of the trunk are more often the affected foci of the comedowns. The excess androgens implicated in male acne is locally depleted by the composition of this invention. Two scrub applications daily, morning and evening have been found to reduce the fulminating acne areas and to reduce the severity of the acne attacks.

I claim:

1. A topical application composition for mitigating male pattern baldness and testosterone-induced acne consisting essentially of

| a) sodium chloride | 2.0 to 5.5% |
|---|---|
| b) lecithin | 0.35 to 3.5% |
| inositol | 0.0 to 3% |
| soy oil | 0.008 to 0.04% |
| phosphoric acid | 0.005 to 0.035% |
| choline chloride | 0.025 to 3.0% |
| c) polysorbate - 80 | 0.3 to 3.0% | the balance a cosmetically acceptable vehicle for topical application.

2. The composition according to claim 1 consisting essentially of

| a) sodium chloride | 3.5 to 4.0% |
|---|---|
| b) lecithin | 1.9 to 2.2% |
| inositol | 0.0 to 0.09% |
| soy oil | 0.016 to 0.033% |
| phosphoric acid | 0.024 to 0.03% |
| choline chloride | 0.12 to 0.35% |
| c) polysorbate -80 | 1.2 to 1.5% | in a cosmetically acceptable vehicle for topical application.

3. The composition according to claim 1 wherein said cosmetically acceptable vehicle is a diluted nonionic shampoo concentrate.

4. The composition according to claim 3 wherein the shampoo concentrate includes nonionic polysorbate-80.

5. The composition according to claim 1 wherein said vehicle comprises an aqueous solution and dispersion of components a), b), and c) wherein said inositol content is absent and said vehicle is formulated with a nonionic non-foaming dispersant.

6. The composition according to claim 5 wherein said non-foaming dispersant is an additional amount of polysorbate-80.

7. A method for mitigating the progression of testosterone-induced topical conditions including acne and male-pattern baldness which comprises the steps of topical application to the affected areas of at least one composition containing the actives according to claim 2.

8. The method according to claim 7 comprising the steps of the initial application of a composition containing said actives formulated in said vehicle as a cleaning shampoo and then a further application of an additional composition containing said actives formulated as a topical skin conditioner with components a) b) and c) dispersed or dissolved in a non-foaming topical vehicle.

9. The method according to claim 7 wherein the male-pattern baldness effects on the scalp are mitigated by applying to the entire scalp, quantities of the shampoo-based composition containing said actives; cleansing said scalp areas/wetted with said shampoo; prolonging said wet contact for at least two minutes; rinsing said shampoo from the scalp, and then applying by wetting the partially dried scalp, a composition containing said actives in a non-foaming conditioning base and then drying said conditioning composition on the scalp.

10. The method according to claim 9 wherein said shampoo formulation has the formula

| | |
|---|---|
| NaCl | 3.82% |
| lecithin | 2.25% |
| inositol | 0.25% |
| soy oil | 0.10% |
| phosphoric acid | 0.25% |
| choline chloride | 0.40% |
| polysorbate -80 | 2.25% |
| nonionic shampoo base | |
| water qs ad | 1.0 liter | and said skin conditioner has the formula

| | |
|---|---|
| NaCl | 3.82% |
| lecithin | 2.78% |
| inositol | 0.25% |
| soy oil | 0.10% |
| phosphoric acid | 0.25% |
| choline chloride | 0.40% |
| polysorbate -80 | 2.25% |
| aqueous vehicle qs ad | 1.0 liter |

11. The method according to claim 7 wherein the effects of testosterone-induced acne are mitigated by the steps comprising application to said acne affected areas of nonionic soap scrub formulation with said actives for cleansing the affected areas; and then rinsing same from said affected areas.

12. The method according to claim 11 wherein said nonionic soap scrub has the formula

| | |
|---|---|
| NaCl | 3.82% |
| lecithin | 2.78% |
| soy oil | 0.10% |
| phosphoric acid | 0.25% |
| choline chloride | 0.40% |
| polysorbate -80 | 2.25% |
| nonionic shampoo base | 35.50% |
| water qs ad | 1.0 liter |

13. The composition according to claim 2 additionally containing, as adjuvants, topically active vitamins selected from the group consisting of vitamin D, Vitamin E, and pantothenic acid.

* * * * *